US012648844B2

(12) United States Patent
Bachmann et al.

(10) Patent No.: US 12,648,844 B2
(45) Date of Patent: Jun. 9, 2026

(54) DEVICE FOR TRANSPLANTING A DESCEMET'S MEMBRANE

(71) Applicant: UNIVERSITÄT ZU KÖLN, Cologne (DE)

(72) Inventors: Bjoern Bachmann, Cologne (DE); Claus Cursiefen, Cologne (DE); Sebastian Siebelmann, Solingen (DE)

(73) Assignee: UNIVERSITAET ZU KOELN, Cologne (DE)

( * ) Notice: Subject to any disclaimer, the term of this patent is extended or adjusted under 35 U.S.C. 154(b) by 935 days.

(21) Appl. No.: 17/435,295

(22) PCT Filed: Mar. 4, 2020

(86) PCT No.: PCT/EP2020/055687
§ 371 (c)(1),
(2) Date: Aug. 31, 2021

(87) PCT Pub. No.: WO2020/178332
PCT Pub. Date: Sep. 10, 2020

(65) Prior Publication Data
US 2022/0151766 A1 May 19, 2022

(30) Foreign Application Priority Data
Mar. 6, 2019 (EP) ..................................... 19161116

(51) Int. Cl.
*A61F 2/14* (2006.01)
*A61F 9/00* (2006.01)
*A61F 9/007* (2006.01)

(52) U.S. Cl.
CPC ............ *A61F 2/148* (2013.01); *A61F 9/0017* (2013.01); *A61F 9/00781* (2013.01)

(58) Field of Classification Search
CPC ...................................................... A61F 2/148
See application file for complete search history.

(56) References Cited

U.S. PATENT DOCUMENTS 4,934,363 A 6/1990 Smith
4,995,889 A 2/1991 Abel et al.
(Continued)

*Primary Examiner* — David H Willse
(74) *Attorney, Agent, or Firm* — Andrew Wilford

(57) ABSTRACT

The invention relates to a device for the transplantation of a Descemet's membrane-endothelium graft (5), comprising a longitudinal tube (1), the tube (1) having an inner cavity (2), an inlet opening (3) at its proximal end (PE) through which it is possible to introduce the graft (5) into the cavity (2), and an outlet opening (4) at its distal end (DE) through which it is possible to eject the graft (5) from the cavity (2), particularly into the anterior eye chamber of a patient, a guiding element (6) situated in the cavity (2) of the tube (1) extending from the proximal end area of the tube (1) or device towards the distal end area of the tube (1) or device and having an increasing cross section at least along a part of its extension, particularly by increasing the width of the guiding element (6) more than the height of the guiding element (6), wherein the guiding element (6) extending beyond the outlet opening (4) of the tube into the exterior environment of the tube (1), and having the distal end (6*b*) of the guiding element (6) being positioned outside of the tube (1) in front of the outlet opening (4) of the tube (1).

13 Claims, 3 Drawing Sheets

(56)  References Cited

U.S. PATENT DOCUMENTS

| | | | | |
|---|---|---|---|---|
| 7,985,197 B2 | 7/2011 | Maeda | | |
| 8,470,029 B2 | 6/2013 | Walter | | |
| 10,874,504 B2 | 12/2020 | Bachmann | | |
| 2017/0252059 A1* | 9/2017 | Shiber | ............ | A61B 17/320758 |
| 2019/0125520 A1* | 5/2019 | Bachmann | .............. | A61F 2/148 |

* cited by examiner

DEVICE FOR TRANSPLANTING A DESCEMET'S MEMBRANE

CROSS REFERENCE TO RELATED APPLICATIONS

This application is the US-national stage of PCT application PCT/EP2020/055687 filed 4 Mar. 2020 and claiming the priority of European patent application 19161116.9 itself filed 6 Mar. 2019.

FIELD OF THE INVENTION

The invention relates to a device for the transplantation of a Descemet's membrane-endothelium graft.

BACKGROUND OF THE INVENTION

Such a tube a longitudinal tube typically has an inner cavity, an inlet opening at its proximal end through which it is possible to introduce the graft into the cavity, and an outlet opening at its distal end through which it is possible to eject the graft from the cavity, particularly into the anterior eye chamber of a patient and a guiding element situated in the cavity of the tube extending from the proximal end area of the tube or device toward the distal end area of the tube or device and having an increasing cross section at least along a part of its extension, particularly by increasing the width of the guiding element in the mentioned part more than the height of the guiding element.

A device of this kind is generally known from the publication WO2018/001558 of the same applicant.

Devices of this type are used as part of an eye surgery referred to as DMEK in order to insert the Descemet's membrane with endothelium originating from a donor eye into a recipient eye, after its affected Descemet's membrane has been removed.

In this kind of surgery, the anterior chamber of the eye is opened with an incision, the affected Descemet's membrane is scraped out and removed, and the donor Descemet's membrane is inserted into the anterior chamber using the device. For that purpose, the outlet opening is inserted through the incision into the eye chamber. Typically, the membrane is handled in its natural relaxed state in which it is wound up to form a single-axis winding.

A single-axis winding is understood here to mean that the membrane surface is wound up around a single axis and, in this case, the end of the membrane that is lying in the winding direction thus lies over the other end of the membrane surface.

Using the device of the mentioned kind it is possible to introduce the membrane in this state of a single-axis winding through the inlet opening into the device and to eject the membrane in an at least partially unrolled state. Such a partially unrolled state is for example understood to comprise a state of the winding having a bigger diameter compared to the initial diameter, meaning that the overlap of the membrane surface is at least reduced or a bent state of the membrane surface with no overlap between the two ends of the membrane lying in the original winding direction or a state in which the membrane is wound-up to a double axis winding. Preferably, the unrolled state is a state in which the predominant part of the membrane surface is essentially flat.

The guiding element in the cavity of the tube essentially extends parallel to the extension of the tube. The middle axis of the tube may be positioned in the guiding element along its extension within the tube. The guiding element is used to guide the membrane in the tube along its way from the inlet to the outlet opening by the fact that the wound-up membrane may be put on the proximal end of the guiding element so that the guiding element is received in the inner free space of the single-axis winding and accordingly the membrane is riding on the guiding element through the tube toward the opening if it is moved forward, for example pushed forward.

The guiding element furthermore facilitates spreading the diameter of the wound up membrane or preferably unrolling of the wound-up membrane at least partially by the increasing cross section of the guiding element that exists at least along a part of its extension, preferably a part near the distal end of the guiding element and/or near the outlet opening. The cross section of the guiding element increases toward the proximal end toward the distal end area of the guiding element so that spreading or unrolling of the membrane automatically takes place if the membrane that surrounds the guiding element is moved toward the distal end of the device. By spreading the inner diameter of the single-axis winding overlapping of the membrane is at least reduced, preferably cancelled.

In the mentioned state of the art the part of the guiding element that increases in cross section is disposed within the tube of the device near the outlet opening. Accordingly, the unrolling of the membrane essentially takes place in the tube and the membrane is inserted into the eye chamber in a state of the membrane that is essentially achieved in the tube.

It is a drawback of the known device that the entire outlet opening of the device needs to be introduced into the anterior eye chamber in order to eject the membrane in the partially unrolled state into this chamber. Even though the known device and also the device of the invention may have at least at its distal outlet opening a flattened cross section of the tube with a height being smaller than the width of the tube, the known device demands to provide a fairly large incision to receive the entire opening.

OBJECTS OF THE INVENTION

It is therefore an object of the present invention to provide a device that may work with a reduced size of the incision or that at least provides less stress to the eye chamber during surgery and preferably that facilitates the introduction of a Descemet's membrane into the anterior chamber of the eye in a DMEK surgery. Furthermore it is an object of the invention to provide more stability to the at least partially unrolled membrane also in the area in front of the outlet opening.

The directions specified in this description preferably refer to an orientation of the device, in which it is used as intended in a typical surgery. In such a DMEK surgery, the patient generally lies on his/her back and looks upward; the optical axis of the eye is thus oriented at least substantially vertically based on the Earth reference frame, which also forms the reference frame for the subsequent specified directions for the device.

Accordingly, the width of the device is regarded in a horizontal direction and perpendicular to the longitudinal extension of the tube of the device, also named lateral. The height is regarded in vertical direction and perpendicular to the longitudinal extension of the tube of the device, i.e. between bottom and top of the device. The details given (top/bottom/lateral) refer to a viewing of the cross section of the device perpendicular to the longitudinal direction of extension of the tube, unless expressly described otherwise. "Distal" or "distal end" refers to the end of the device or respective element that is facing toward the eye during a surgery or is near the eye. "Proximal" or "proximal end" refers to the end of the device or element that is facing away from the eye or is far from the eye during a surgery.

SUMMARY OF THE INVENTION

The mentioned object is by the guiding element extending beyond the outlet opening of the tube into the exterior environment of the tube, and having the distal end of the guiding element being positioned outside of the tube in front of the outlet opening of the tube.

Preferably the guiding element, in particular the distal end of the guiding element outside of the tube and in front of the outlet opening is integrally formed or formed in one piece with the entire device, for example by die casting or injection molding or 3D-printing. In a case in which the guiding element and the tube of the device will be separately produced the invention may provide that these two parts are connected by fusing, gluing or any other kind to form a unitary one-piece construction of the device. At least in this embodiment, preferably in any case the entire guiding element has a stationary position relative to the tube.

According to another embodiment the guiding element may be formed as an element separate from the tube of the device. In this embodiment the guiding element and the tube may be also separate non-connected elements during a surgery, but it is preferred in this embodiment that the guiding element and the tube are at least temporarily connectable, for example during surgery. The mentioned embodiment provides the possibility to mount the wound-up membrane on the proximal end of the guiding element in a state in which the guiding element is not yet introduced into the tube. After mounting the membrane to the guiding element the guiding element may be inserted into the tube, particularly through either end, preferably so that after insertion the membrane is protected by the tube when moving the membrane on the guiding element.

Accordingly, the membrane may be safely handled during a surgery. Even in this embodiment of separate elements the device of the invention is formed if the guiding element is situated in the tube and extends with its distal end beyond the outlet opening of the tube.

In order to facilitate a stable position between the tube and the guiding element the invention may provide, that the guiding element may be at least temporarily connected to the tube as mentioned before. Such a connection may be realized between the guiding element and the tube by a mechanical locking mechanism established between these elements, for example a form-fitting and or force-fitting linking/locking mechanism. The mechanical connection between the guiding element and the tube may also be realized by magnets on both elements attracting each other.

The preferably releasable connection between the guiding element and the tube may be established at the distal end of the tube or proximal end of the tube or between the tube ends. The connection between the guiding element and the tube may provide that the guiding element may be moved relative to the tube, preferably may be fixed in a selected position after moving.

The tube or device can be composed of any material, for example a plastic material, particularly a polymer, preferably of PTFE (polytetrafluoroethylene) in whole or in subregions.

The invention provides that a guiding of the at least partially unrolled membrane by the guiding element also takes place after the membrane has left the tube of the device. The distal end of the guiding element that is positioned outside of the tube and in front of the outlet opening of the tube may be partially inserted through the incision into the eye chamber. In contrast to the state of the art the outlet opening need not be forwarded through the incision into the eye chamber even though this is also possible.

Preferably the height of the distal end of the device comprising the distal end of the guiding element is smaller than the height of the device at the position of the outlet opening. Accordingly the incision may be made smaller compared to known devices or is at least less stressed by the device during a surgery.

Preferably the position of the outlet opening of the tube of the device is understood to be the most distal position on the longitudinal middle axis of a cross sectional plane intersecting this longitudinal axis of the tube wherein the cross sectional view of the tube in this plane is totally closed in the circumferential direction, i.e. the tube has at this most distal position a closed tubular wall extending over 360 degrees. The mentioned plane comprising the outlet opening may be oriented perpendicular to the axis of the longitudinal extension of the tube, but this plane preferably may also be inclined to a perpendicular plane. Accordingly, in this plane the outlet opening always forms a closed line.

According to a preferred embodiment of the invention the guiding element is increasing in width outside the tube in front of the outlet opening of the tube, regarded in a direction from the outlet opening toward the distal tip of the distal end of the guiding element. This increase in width toward the distal tip is given at least in a part of the extension of the distal end of the guiding element.

Preferably, the distal tip of the guiding element is understood to be the absolute end of the device, whereas the distal end of the guiding element comprises a longitudinally extended portion of the guiding element between the outlet opening of the tube and the mentioned distal tip. This longitudinally extended portion of the guiding element comprises the mentioned part which is increasing in width.

Furthermore preferred the distal end of the guiding element that is positioned outside the tube and in front of the outlet opening increases in width up to the maximum width (regarded in lateral/horizontal direction and perpendicular to the longitudinal extension of the tube/guiding element) of the entire guiding element.

The position of the maximum width may accordingly be positioned between the outlet opening and the distal tip of the guiding element.

Such an increase in width of the guiding element in the area outside the tube and in front of the outlet opening provides that the membrane is further unrolled by the guiding element even though the membrane has already left the tube. This provides more unrolling activity of the invention compared to the state of the art since in the invention the maximum width of the guiding element is not limited by the cross section of the tube.

Preferably, the membrane is guided essentially below the guiding element, at least in the region of the distal end of the guiding element. This is for example achieved if the overlapping portion of the wound-up membrane is positioned at the top of the single-axis winding of the membrane if it is guided on the guiding element. The spreading in diameter of the winding that is performed by the increasing cross section/width of the guiding element then results in a repositioning of the membrane surface toward the bottom part of the guiding element.

The maximum width of the distal end of the guiding element outside the tube in front of the outlet opening provides that the membrane reaches its maximum unrolled state in front of the outlet opening, in particular in the anterior eye chamber.

A preferred improvement of the invention furthermore provides that the distal end of the guiding element decreases in width from the position of the maximum width toward the distal tip of the guiding element. Such a tapered tip of the distal end of the guiding element facilitates to open the incision for inserting the remaining part of the distal end of the guiding element into the anterior eye chamber.

The shape of the distal end of the guiding element in a horizontal cross sectional plane between the position of the maximum width and the distal tip may for example have the configuration of a semi-circle or may comprise at least one or exactly one stepwise reduction in width. At the position of the stepwise reduction in width the gradient of the width regarded along the part of the distal end that decreases in width may have its minimum negative value, particularly being surrounded by larger gradient values (in the understanding that −1 is a larger value than −2). In a possible embodiment the gradient may be minus infinite, particularly thus forming a frontal face of the distal end of the guiding element regarded in a horizontal cross sectional plane being perpendicular to the longitudinal extension of the guiding element.

The distal end of the guiding element may also comprise between the position of maximum width and the distal tip a position in which the gradient of the width has a negative local maximum, being surrounded by smaller (negative) gradient values, particularly meaning that at this position the width is decreasing with a smaller rate.

According to a first preferred embodiment the distal end of the guiding element outside of the tube is connected or at least connectable to the tube at the upper frontal area of the tube wall at the outlet opening or at the upper exterior surface of the tube wall.

Such a connection may be formed by a protrusion protruding upward from an upper surface area, preferably an upper middle surface area of the distal end of the guiding element, particularly the middle surface area being regarded with respect to the width of the distal end. The connection between this protrusion and the upper frontal area of the tube wall at the outlet opening or the upper exterior surface of the tube wall may be a fixed connection or a releasable connection.

Even more preferred the device has a decreasing height of the distal end of the guiding element, particularly of the connecting protrusion regarded from the outlet opening toward the tip of the guiding element. This means that the distal end of the guiding element is tapered in height toward the distal tip.

The guiding element furthermore may be freely floating within the inner free cross section of the cavity of the tube, particularly without any connection to the inner tube wall along the entire extension of the guiding element in the tube. This means that the guiding element is solely connected to the tube on the exterior surface of the tube by means of the distal end of the guiding element, preferably by means the mentioned protrusion of it lying outside the tube.

In addition the guiding element may also be freely floating within the projection of the inner free cross section of the cavity at least in a part of its extension in an area in front of the outlet opening outside the tube.

In order to achieve this the guiding element may have a bent distal end. The guiding element may be understood to originate at the upper frontal area of the tube wall at the outlet opening or at the upper exterior surface of the tube wall, starting its extension, preferably tapered in height toward the distal tip of the distal end and being bent back, preferably by at least essentially 180 degrees, in order to extend into the outlet opening and passing through the tube at least partially.

According to a second embodiment the guiding element may be connected in its upper area to the upper inner wall of the tube, particularly along the majority of the length of the tube. Such a connection provides a more stiff construction of the guiding element and the tube and facilitates to separate the overlapping surface parts of the wound-up membrane already in the tube. This connection may also be a fixed one or may be releasable.

In such an embodiment the distal end of the guiding element outside the tube and in front of the outlet may have no connection to the tube at the upper frontal area of the tube wall at the outlet opening or at the upper exterior surface of the tube wall, particularly providing that the distal end of the guiding element is freely floating within the projection of the inner free cross section of the cavity in front of the outlet opening outside the tube.

The mentioned second embodiment may also be combined with the construction according to which the distal end of the guiding element outside of the tube is connected to the tube at the upper frontal area of the tube wall at the outlet opening or at the upper exterior surface of the tube wall, for example by means of the protrusion as mentioned in connection with the first embodiment.

In all possible embodiments and as already mentioned in the introduction the device may preferably be designed such that the tube has at least in the region of the outlet opening, possibly across its entire extent, a flattened outer cross section (viewed perpendicularly to the direction of extension). The nature of the flattening is preferably such that the tube has a smaller cross-sectional extent in the vertical direction (height) than in the horizontal direction (width), and is preferably oval or elliptic. Preferably, the ratio of vertical extent to horizontal extent, or of height to width, can be in the range of values from 0.5 to 0.8. This is advantageous because the at least partially unrolled membrane is oriented with its major surface area in a horizontal plane that corresponds to the orientation of the incision in the eye to open the anterior eye chamber.

In a possible embodiment the guiding element may have a part along its extension in the tube that has a constant cross section/width. It is possible that the part of the guiding element that increases in width is situated solely outside the tube and in front of the outlet opening, preferably wherein the entire part of the guiding element which is positioned in the cavity of the tube has a constant cross section.

Preferably the guiding element starts in the cavity of the tube to increase in width toward its distal end. The gradient of the width regarded along the extension of the guiding element may also increase toward the distal end, preferably having its maximum positive value in the vicinity of the outlet opening or outside the tube in front of the outlet opening.

According to another preferred improvement the guiding element forms a spike at its proximal end, particularly for feeding a wound-up membrane onto the spike. Preferably the proximal end of the guiding element is in this case situated outside of the tube in front of the inlet opening of the tube.

The mentioned spike may be furthermore freely floating in the cavity of the tube at the position of the inlet opening of the tube, particularly having no connection to the inner tube wall in the inlet opening.

These constructions facilitate to mount the membrane onto the guiding element near the inlet opening in the state of a single axis winding. The one winding axis of the membrane preferably lies on or near the central axis of the tube and/or within the cross section of the proximal end/ spike of the guiding element According to another preferred improvement a lower surface of the inner tube wall extends beyond the outlet opening of the tube toward the external environment of the tube and forming an exterior support surface lying in a distance under the distal end of the guiding element. A slit is formed between the exterior support surface and the lower surface of the distal end of the guiding element, particularly the slit is configured for receiving the at least predominantly unrolled Descemet's membrane-endothelium graft after leaving the outlet opening. The membrane is then fully stabilized between the opposing surface of the slit, namely the bottom surface of the distal end of the guiding element and the support surface.

The support surface and the lower/bottom surface of the distal end of the guiding element may be shaped convex to each other, particularly meaning the support surface changes it shape from convex to concave (relative to the bottom surface of the distal end of the guiding element) toward the outlet opening.

Furthermore, the device may comprise an upward open gutter outside the tube in front of the inlet opening, the bottom of the gutter merging into the inner wall of the cavity of the tube. The gutter may have an increasing height from the proximal end of the device toward the inlet opening of the tube. Such a gutter may be positioned under at least a part of the spike formed at the proximal end of the guiding element. Accordingly, the gutter facilitates to mount the wound-up membrane from the top to the spike.

It can be further envisaged in the invention that at least the end of the tube with the inlet end has a connection interface for a syringe, for example a standard "Luer-Lock." This makes it possible for the membrane to be flushed out of the device and simultaneously unrolled by means of a liquid. By means of the Luer-Lock the device may be connected to an apparatus for facilitating the ejection of the membrane out of the device, for example to an irrigation-aspiration system or a phako system.

In a supplemental embodiment, it can be envisaged in the device that a passage, especially a passage which extends axially at least regionally, is arranged on or in the tube, in particular with the passage opening, at the outlet opening, into the edge end face of the tube. At every point, such a passage can be arranged preferably within the wall thickness of the tube and particularly preferably in the outlet end face of the tube. In a particularly preferred embodiment, such a passage is arranged in the lower region of the tube, especially in the support surface underlying the distal end of the guiding element.

There is thus the possibility of being able to put an air bubble, by means of the passage, under the membrane inserted into the eye anterior chamber, by the surgeon pushing air through the passage, for example by means of a syringe. Especially when the mouth opening of the passage lies below the membrane, a thus generated air bubble automatically lies under the membrane and pushes this membrane upward. Preferably, the passage can, toward the inlet opening or at this opening, merge into a piece of tubing lying beyond the tube. At such a piece of tubing, it is, for example, possible to connect a syringe.

BRIEF DESCRIPTION OF THE DRAWING

The invention will be described on the basis of the following figures showing different sectional views of the preferred embodiments. These sectional views depict the qualitative behavior of the essential features of the inventions. It is not claimed that the sectional views show a correct scaling in their details. More particularly:

SPECIFIC DESCRIPTION OF THE INVENTION

In all the figures LV depicts a sectional view of the device in a vertical plane comprising a longitudinal axis, preferably the longitudinal middle axis MA of the device. LH depicts a sectional view of the device in a horizontal plane comprising a longitudinal axis, preferably the longitudinal middle axis MA of the device. CSn depict cross sectional views in planes perpendicular to a longitudinal axis, preferably the longitudinal middle axis MA of the device on n different positions of this longitudinal axis.

Figure 1:
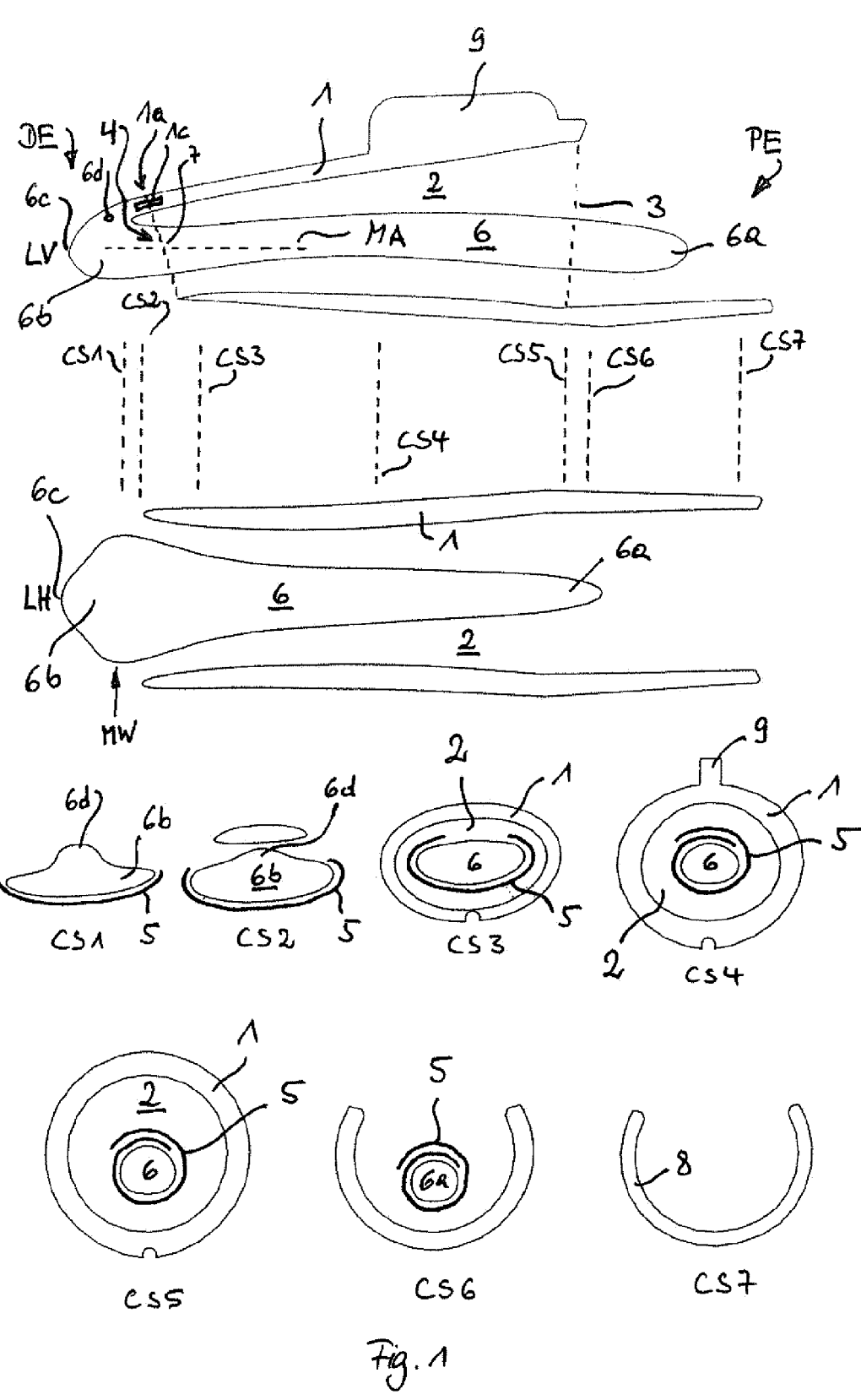
FIG. 1 shows various longitudinal and cross sections of a first embodiment of the invention.

FIG. 1 shows a first embodiment of a device for the transplantation of a Descemet's membrane. According to the view LV and LH and the cross sectional views CS3, CS4 and CS5 the device comprises a tube 1 having an inner cavity 2, an inlet opening 3 at the proximal end of the tube and an outlet opening 4 at the distal end of the tube 1.

It is possible to introduce a Descemet's membrane endothelium graft 5 through the inlet opening 3 into the device. The graft 5 is placed in the state of a single axis winding around the spike 6a of a guiding element 6. This guiding element 6 is situated in the cavity 2 of the tube 1 and extends from the proximal end PE of the device toward the distal end DE of the device. Particularly, in this embodiment the guiding element 6 extends from an area in front of the inlet opening 3 beyond the outlet opening 4, regarded toward the intended movement of the graft 5 from the inlet opening 3 to the outlet opening 4. Accordingly, the guiding element 6 is longer than the length of the tube 1 and projects out of the tube 1 on both ends of the tube 1.

The guiding element is increasing in cross section toward the distal end of the device. This is particularly done by increasing the width of the guiding element 6 (regarded in the horizontal plane, see LH) more than the height of the guiding element 6 (regarded in the vertical plane, see LV). This increase of the cross section and particularly of the width of the guiding element 6 performs a spreading of the diameter and a partial unrolling of the graft 5 as can be seen in the different cross sectional views CS6 to CS1. After introducing the wound-up graft 5 into the inlet opening 3 the overlap of the ends of the membrane lying in the winding direction is positioned on top of the winding. When the graft 5 leaves the outlet opening 4 after passing through the tube 1 the predominantly unrolled graft is essentially positioned underneath the guiding element 6, particularly underneath the distal end 6b of the guiding element 6 which is positioned outside of the tube 1 in front of the outlet opening 4.

Essentially the view LH shows that the guiding element that extends through the tube 1 beyond the outlet opening 4 reaches its maximum width MW in its distal end 6b that is positioned behind the outlet opening when regarded toward the intended movement of the graft through the device. Accordingly the graft 5 reaches its most unrolled state outside the tube.

Regarded again toward the intended movement of the graft 5, i.e. toward the distal tip 6*c* of the distal end 6*b* the distal end 6*b* is decreasing in width and preferably also in height. This facilitates to introduce the distal end 6*b* of the guiding element 6 into the incision of the anterior eye chamber for introducing the at least partially, preferably predominantly unrolled graft 5 into this chamber.

In this embodiment of FIG. 1 the guiding element 6 is totally free floating in the inner cavity of the tube 1, meaning that there is absolutely no connection between the guiding element 6 and the inner wall of the tube 1. As can be seen particularly in the view LV the guiding element 6 is solely connected to the tube 1 at the upper end face/frontal area of the tubular wall with the exterior part of the guiding element forming its distal end 6*b*.

To perform this connection the distal end 6*b* of the guiding element 6 comprises a protrusion 6*d* protruding upward and merging into the end face/frontal area 1 *a* of the tube 1. By integrally merging into the end face 1 *a* this connection is a fixed connection and accordingly the guiding element 6 and the tube integrally formed as one piece.

In an alternative embodiment the connection between the protrusion and the tube at its front face 1 *a* may also be releasable, for example by a magnetic connection or a locking means 1 *c*. In this embodiment the guiding element 6 and the tube 1 are separate elements that may be connected to each other at least temporarily, for example during surgery.

The guiding element 6 or particularly at least the distal end 6*b* of it may be understood to have a shape in front of the outlet opening 4 outside the tube 1 in the vertical plane as seen in the view LV that is essentially bent by 150 to 180 degrees.

Furthermore in this particular embodiment and shown by the view CS2 the guiding element and its distal end is also free floating in the projection of the outlet opening or the inner free cross section of the tube cavity at least in a part of its extension outside the tube and in front of the outlet opening, proving that the guiding element is passing though the outlet opening 4 without contacting the inner tubular wall in this outlet opening.

The outlet opening 4 is arranged in a plane inclined with respect to the plane perpendicular to the middle axis MA. The position 7 of the outlet opening 4 may be understood to be the intersection between the middle axis MA and the plane of the outlet opening 4 shown in the view LV as a dashed line. In this plane the section of the tube 1 shows a totally closed circumferential line, comparable to the view CS3.

In addition FIG. 1 shows that the device comprises a gutter 8 in front of the inlet opening 3, regarded toward movement of the graft 5. The gutter that is open toward the top area of the device facilitates mounting the wound-up graft on the spike 6*a* of the guiding element 6.

Furthermore, FIG. 1 depicts a handle 9 on top of the tube 1 of the device for an easy handling of the device by a surgeon.

Figure 2:
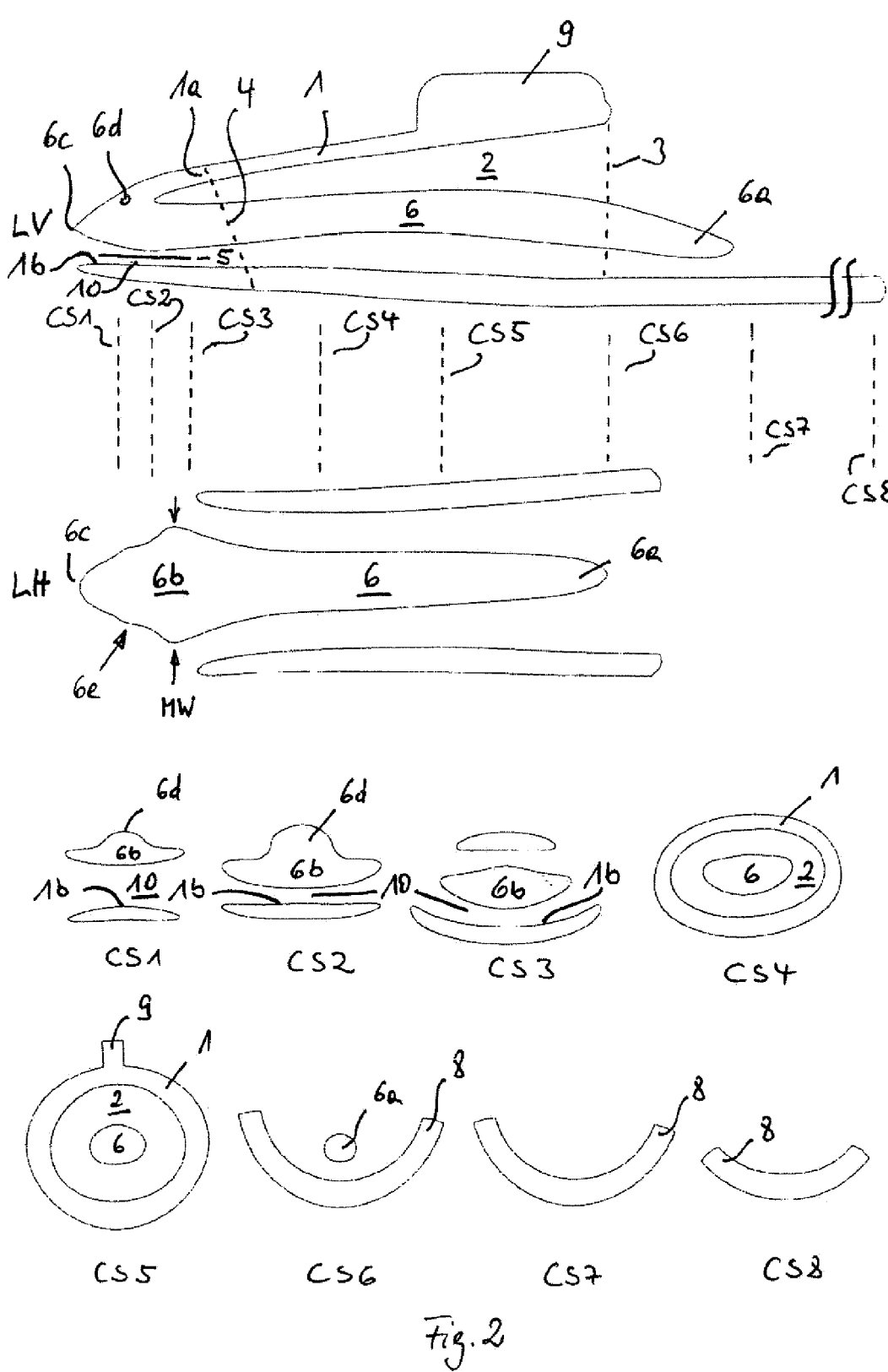
FIG. 2 shows various longitudinal and cross sections of a second embodiment of the invention.

With regard to FIG. 2 only the essential inventive differences to FIG. 1 are described. All other elements to which no differences are explained are constructed as shown and described in FIG. 1.

As can be seen here in views CS8 to CS6 the height of the gutter 8 is increasing in the direction from the proximal end PE toward the inlet opening 3.

An even more essential difference to FIG. 1 is that in the embodiment of FIG. 2 the lower surface of the inner tube wall regarded form the outlet opening 4 toward the distal end of the device is extending beyond the outlet opening thus forming an exterior support surface 1 *b* lying underneath the distal end 6*b* of the guiding element 6. Accordingly, between the support surface 1 *b* and the lower surface of the distal end 6*b* of the guiding element a slit 10 is formed that receives the graft and stabilizes the predominantly unrolled graft 5 after ejecting out of the outlet opening 4. In FIG. 2 the graft 5 is only shown in the view LV positioned in the mentioned slit 10.

As can be seen in the view CS1 the support surface 1 *b* is convex shaped relative to the bottom surface of the distal end 6*b* of the guiding element, whereas the same support surface 1 *b* is shaped concave in the view CS3. This implies a change in shape from convex to concave in a direction toward the outlet opening 4.

Also in this embodiment of FIG. 2 the guiding element 6 is totally free floating in the inner cavity 2 of the tube 1 and solely connected to the upper end face 1 *a* of the tubular wall. Accordingly also here the distal end 6*b* forms a bent part of the guiding element 6 that passes through the outlet opening 4 into the cavity without any connection to the inner tubular wall.

The view LH furthermore shows that the decrease of the width between the position of maximum width MW and the distal tip 6*c* is performed with a locally smaller rate, Particularly in the middle between these two positions, thus forming an undulation/bulge in the tapered front face of the guiding element. At the position of this bulge 6*e* the gradient of the width has a local maximum with negative sign.

Figure 3:
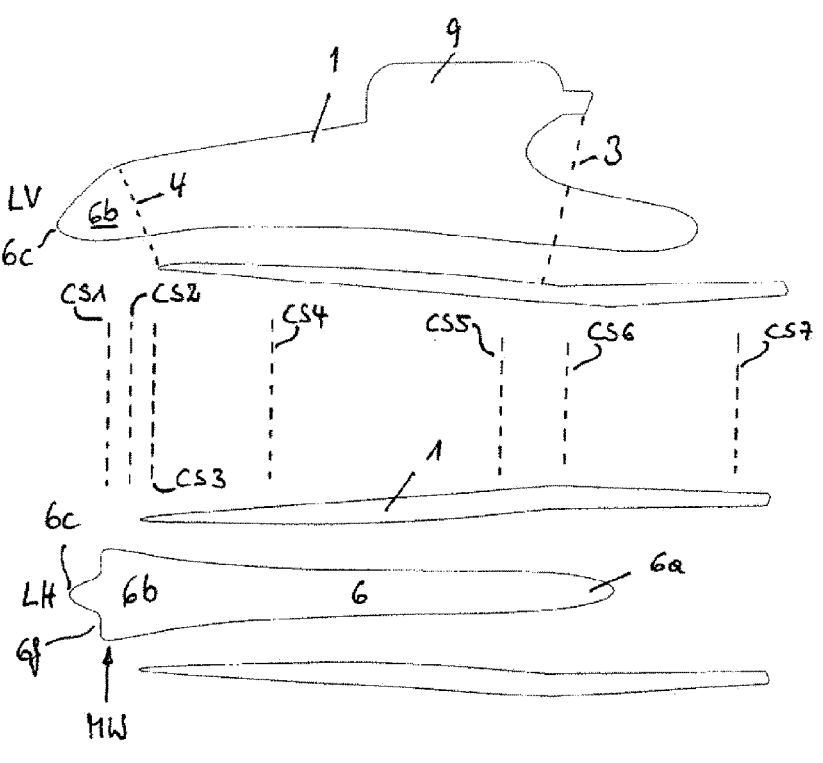
FIG. 3 shows various longitudinal and cross sections of a third embodiment of the invention.

In FIG. 3 a third embodiment is shown. Again only the essential differences to FIG. 1 are explained. In this embodiment the guiding element 6 is connected in its upper area, that forms a protrusion 6*c*, to the inner upper wall of the tube 1. This connection is given along the majority of the length of the guiding element in the tube 1. Only the proximal end 6*a* of the guiding element 6 forms a free floating spike for mounting the wound-up graft as shown in the view CS6.

On its way through the tube 1 the wound up graft 5 is unrolled at a very early stage that can be seen in the view CS5. The upward protruding part 6*c* of the guiding element 6 effects a separation of the overlapping end of the membrane graft 5 thus cancelling the overlap. The graft 5 is still wound around the guiding element 6 until it has left the outlet opening and reaches the maximum width of the guiding element 6 at its distal end 6*b*.

Also in this embodiment the guiding element 6 extends beyond the outlet opening 4 and forms an external distal end 6*b* outside the tube and in front of this outlet opening 4. Comparable to FIG. 1 also the distal end 6*b* of the guiding element forms a protrusion 6*c* that is connected to the end face of the tube 1.

The guiding element 6 reaches in its distal end 6*b* the maximum width at position MW. Between this position MW and the distal tip 6*c* the distal end is stepwise decreased in width and forms in this horizontal sectional view a frontal face 6*f* that is oriented perpendicular to the longitudinal extension of the tube 1/guiding element 6 or device. Accordingly, at this step or front face 6*f* the gradient of the width regarded along the longitudinal extension reaches its local minimum value, for example in this case minus infinity.

Figure 4:
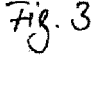
FIG. 4 shows the cross sectional view LH of a device in the horizontal plane.
Figure 4:
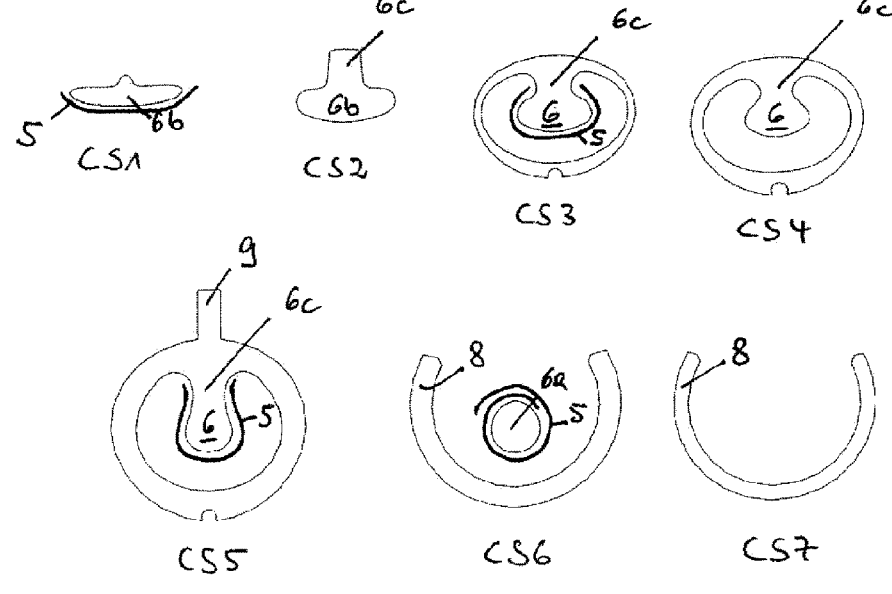
Figure 4:
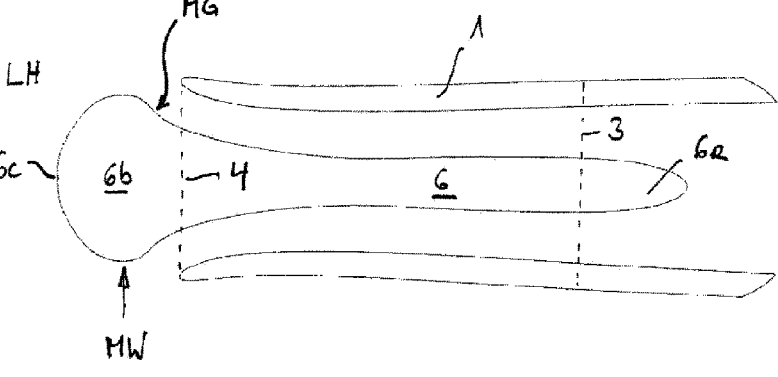

FIG. 4 just shows the cross sectional view LH of a device in the horizontal plane to depict another inventive shape of the distal end 6*b* of the guiding element 6.

The construction in the vertical plane can be as described in the other figures.

In this cross sectional view LH the distal end 6*b* is shaped in the area between maximum width MW and distal tip 6*c* essentially semi-circular.

The increase in width of the guiding element along its extension reaches its maximum rate, namely the maximum (positive) gradient of the width at the position referred as MG. This position is outside the tube 1 in front of the outlet opening 4.

FIGS. 1 to 4 show an orientation of the device in a typical surgery with a patient lying on his back and looking upward so that the optical axis of the eye is vertically oriented. It may come up the need to use the device in an inverted orientation in which top and bottom are exchanged. Nonetheless also the inverted device shows the features as described before.

The invention claimed is:

1. A device for the transplantation of a Descemet's membrane-endothelium graft, the device comprising:
a longitudinal tube having
    a proximal end,
    an opposite distal end,
    an inner cavity,
    an inlet opening at the proximal end through which it is possible to introduce the graft into the cavity, and
    an outlet opening at the distal end through which it is possible to eject the graft from the cavity into an anterior eye chamber of a patient, and
an elongated guiding element in the cavity of the tube, formed unitarily with the tube, having a predetermined length, extending from the proximal end of the tube toward the distal end of the tube, and having a cross section increasing toward the distal end at least along a part of the predetermined length with a corresponding increase in a width of the guiding element more than a height of the guiding element at the distal end of the tube adjacent the outlet opening, the guiding element extending beyond the outlet opening of the tube externally of the tube, a distal end of the guiding element being outside of the tube in front of the outlet opening of the tube, whereby a Descemet's membrane wound around the guiding element is unwound when moved along the guiding element toward the outlet end; and
an upwardly open gutter outside the tube in front of the inlet opening and having a floor merging into an inner wall surface of the cavity of the tube.

2. The device according to claim 1, wherein a width of the guiding element increases up to a maximum width of the guiding element in front of the outlet opening of the tube.

3. The device according to claim 2, wherein the width of the guiding element tapers from the maximum width toward the distal end of the guiding element.

4. The device according to claim 1, wherein the distal end of the guiding element outside of the tube is connected to the tube at an upper frontal area of the tube at the outlet opening or at an upper exterior surface of the tube.

5. The device according to claim 4, wherein the connection between the guiding element and the tube is formed by a protrusion protruding upward from an upper middle surface area of the distal end seen widthwise at a middle surface area with respect to the width of the distal end of the guiding element.

6. The device according to claim 5, wherein a height of the connection decreases from the outlet opening toward a tip of the guiding element.

7. The device according to claim 4, wherein the guiding element is freely floating within an inner free cross section of the cavity without any connection to an inner wall surface along the tube and along a full length of the guiding element in the tube.

8. The device according to claim 1, wherein the guiding element is connected in an upper area to an upper inner wall surface of the tube along the majority of a length of the tube.

9. The device according to claim 1, wherein the guiding element is formed with a spike at a proximal end for feeding a wound-up membrane onto the spike, the proximal end being situated outside of the tube in front of the inlet opening of the tube.

10. The device according to claim 9, wherein the spike is freely floating in the cavity of the tube at the position of the inlet opening of the tube and has no connection to an inner wall of the tube in the inlet opening.

11. The device according to claim 1, wherein a lower inner surface of the tube extends beyond the outlet opening of the tube externally of the tube and forms an exterior support surface lying at a spacing below the distal end of the guiding element.

12. The device according to claim 11, wherein a slit is formed between the exterior support surface and a lower surface of the distal end of the guiding element, the slit being configured for receiving an at least predominantly unrolled Descemet's membrane-endothelium graft after leaving the outlet opening.

13. The device according to claim 1, wherein the gutter has an increasing height from a proximal end toward the inlet opening of the tube.

\*    \*    \*    \*    \*